United States Patent
Picardo et al.

(10) Patent No.: US 6,662,056 B2
(45) Date of Patent: Dec. 9, 2003

(54) CARTRIDGE FOR STORING AN ELECTRODE PAD

(75) Inventors: Anthony G. Picardo, Tacoma, WA (US); Christine Janae, Seattle, WA (US); Thomas Solosko, Issaquah, WA (US); Steven T. Mydynski, Clinton, WA (US); Ian G. MacDuff, Bothell, WA (US); Jon M. Bishay, Woodinville, WA (US); Kent W. Leyde, Redmond, WA (US); Carlton B. Morgan, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/852,431

(22) Filed: May 9, 2001

(65) Prior Publication Data

US 2002/0082644 A1 Jun. 27, 2002

Related U.S. Application Data

(63) Continuation of application No. 09/746,123, filed on Dec. 22, 2000, now abandoned.

(51) Int. Cl.[7] .............................. A61N 1/04; A61B 19/02
(52) U.S. Cl. ........................................ 607/142; 206/438
(58) Field of Search ................................. 206/210, 363, 206/370, 438, 570, 567–571, 557–565, 828; 439/909; 600/372, 382, 386, 391–393; 607/1–2, 115, 142, 148–149, 152–153, 4–5; D3/203

(56) References Cited

U.S. PATENT DOCUMENTS

| | | | | |
|---|---|---|---|---|
| 3,904,074 A | * | 9/1975 | Hoffman et al. | 220/258.3 |
| 5,246,109 A | * | 9/1993 | Markle et al. | 206/363 |
| 5,462,157 A | * | 10/1995 | Freeman et al. | 206/210 |
| 5,464,428 A | * | 11/1995 | Hill | 607/1 |
| 5,607,454 A | | 3/1997 | Cameron et al. | |
| 5,645,571 A | | 7/1997 | Olson et al. | |
| 5,735,879 A | | 4/1998 | Gliner et al. | |
| 5,836,993 A | | 11/1998 | Cole | |
| 5,868,794 A | * | 2/1999 | Barkley et al. | 607/29 |
| 5,879,374 A | | 3/1999 | Powers et al. | |
| 6,142,305 A | * | 11/2000 | Sembach | 206/438 |
| 6,293,962 B1 | * | 9/2001 | Bishay | 607/1 |
| 6,397,104 B1 | * | 5/2002 | Miller et al. | 607/5 |

* cited by examiner

Primary Examiner—Kennedy Schaetzle
Assistant Examiner—Kristen Droesch (57) ABSTRACT

A cartridge is provided for storing one or more electrode pads such as a defibrillator electrode pad. The cartridge includes a housing having a rigid portion, a storage space disposed within the housing, and a storage-space opening that allows one to remove/insert the electrode pad or pads from/into the storage space. Because it has a housing with a rigid portion, such a cartridge can better protect one or more electrode pads from handling damage. Furthermore, one can construct the cartridge such that it is attachable to a medical device such as an AED. This allows an operator to carry or store the medical device, cartridge, and one or more electrode pads as a single unit. In addition, one can construct the cartridge such that the one or more electrode pads can be pre-connected to the medical device. This can eliminate connecting the one or more electrode pads to the medical device during an emergency.

11 Claims, 8 Drawing Sheets

CARTRIDGE FOR STORING AN ELECTRODE PAD

CROSS REFERENCE TO RELATED APPLICATION

This is a continuation of application Ser. No. 09/746,123 file on Dec. 22, 2000 now abandoned.

BACKGROUND OF THE INVENTION

1. Field of the Invention

The invention relates generally to electrode pads, and more particularly to a cartridge for storing one or more electrode pads of a medical device such as an automatic or semi-automatic external defibrillator (AED). In one embodiment of the invention, at least a portion of the cartridge is rigid so that the cartridge protects the one or more electrode pads from damage caused, e.g., by jostling and crushing.

2. Description of the Prior Art

AEDs have saved many lives in non-hospital settings and, as a result of advances in AED technology, the number of lives saved per year is rising. Typically, an AED analyzes a patient's heart rhythm and instructs an operator to administer an electrical shock to the patient if appropriate. For example, a shock can often revive a patient who is experiencing ventricular fibrillation (VF). Because older models of defibrillators include only basic diagnostic and safety features, they are often difficult to operate. Therefore, only specially trained persons such as emergency medical technicians (EMTs) can use these older models to administer shocks to patients. Newer models, however, often include advanced diagnostic and safety features that allow minimally trained persons to administer shocks to patients. Consequently, more people are using AEDs to save lives.

Minimizing time to AED deployment is critical. Once a person goes into sudden cardiac arrest, every minute counts. An AED operator should be able to set up and use an AED to shock a patient within seconds after the operator arrives at the scene. Statistically, for each minute that a person is in cardiac arrest, his/her chance of survival decreases by 10%. And in most cases, there is no chance for resuscitation after 10 minutes. And, even in the best of circumstances, it can take a few minutes to retrieve the AED and a few additional minutes for the AED to diagnose and shock the patient. Therefore, even if the patient is discovered immediately, the operator often has little time to attach the defibrillator electrode pads to the patient, connect the pads to the AED, and activate the AED without further decreasing the patient's chance of survival. Clearly, the faster the operator can set up and activate the AED, the better the chances that the patient will survive.

Figure 1:
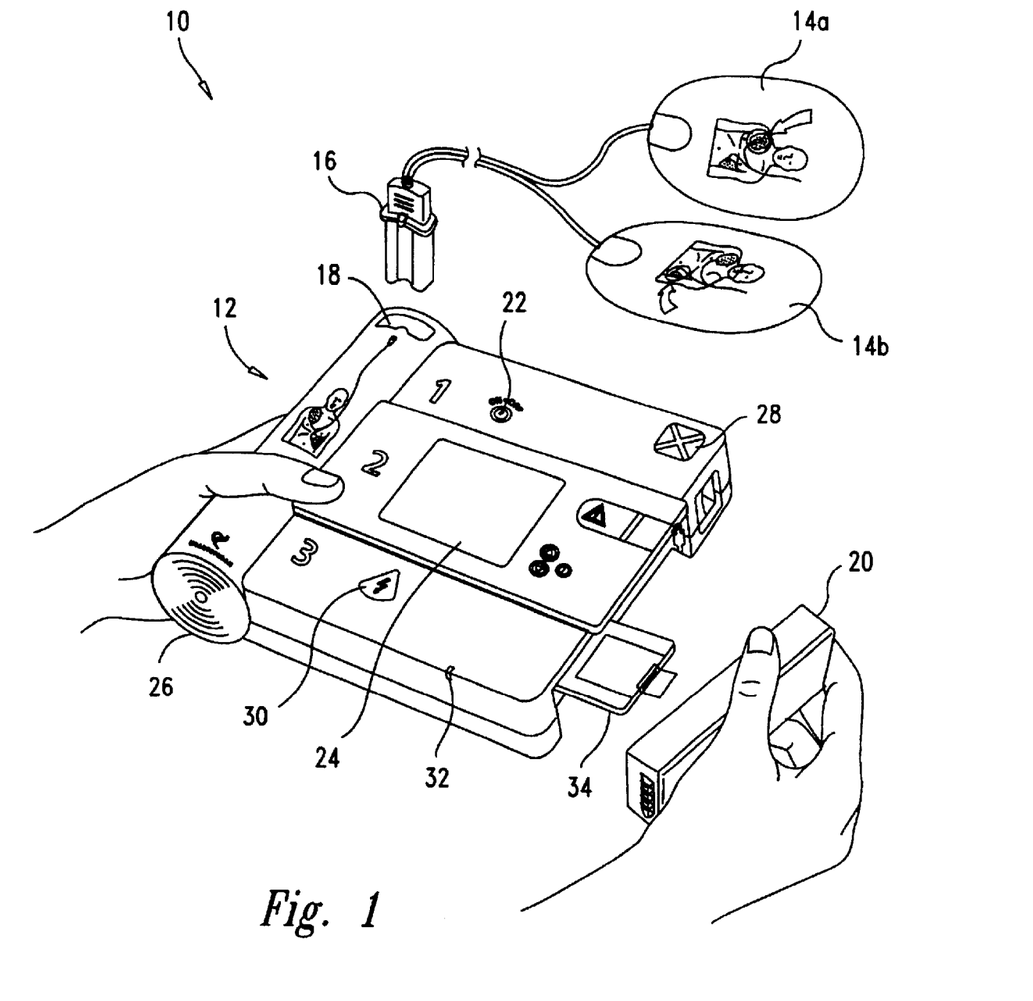
FIG. 1 is a perspective view of a conventional AED system.

FIG. 1 is a perspective view of a conventional AED system 10, which includes an AED 12 for generating a shock and which includes defibrillator electrode pads 14a and 14b for providing the shock to a patient (not shown in FIG. 1). A connector 16 couples the electrode pads 14a and 14b to a receptacle 18 of the AED 12. Typically, the electrode pads 14a and 14b are sealed within a flexible, i.e., soft, package (not shown in FIG. 1) that an operator (hands shown in FIG. 1) tears or peels open to access the electrode pads. The package acts as a moisture barrier that prevents the electrode-pad contact gel (not shown) from drying out during storage of the electrode pads 14a and 14b. Because it is not affected by moisture loss, the connector 16 need not be—but can be—sealed within the package.

The AED 12 may include a battery 20 for supplying power, a main on/off key switch 22, a display 24 for displaying operator instructions, cardiac waveforms, or other information, a speaker 26 for providing audible operator instructions, an AED status indicator 28, and a shock button 30, which the operator presses to deliver a shock to the patient. The AED 12 may also include a microphone 32 for recording the operator's voice and other audible sounds that occur during the rescue, and a data card 34 for storing these sounds along with the patient's ECG and a record of AED events for later study.

Still referring to FIG. 1, during an emergency where it is determined that the patient may need a shock, the operator retrieves the AED 12 and installs the battery 20 if it is not already installed. Next, the operator removes the electrode pads 14a and 14b from the protective package and inserts the connector 16 into the receptacle 18. Then, the operator turns the on/off switch 22 to the "on" position to activate the AED 12. Following the instructions displayed on the display 24 or "spoken" via the speaker 26, the operator places the electrode pads 14a and 14b on the patient in the respective positions shown in the pictures on the electrode pads and on the AED 12. After the operator places the electrode pads 14a and 14b on the patient, the AED 12 analyzes the patient's ECG to determine whether the patient is suffering from a shockable heart rhythm. If the AED 12 determines that the patient is suffering from a shockable heart rhythm, then it instructs the operator to depress the shock button 30 to deliver a shock to the patient. Conversely, if the AED 12 determines that the patient is not suffering from a shockable heart rhythm, it informs the operator to seek appropriate non-shock treatment for the patient. Furthermore, if the AED 12 determines that the patient is not suffering from a shockable heart rhythm, then it often disables the shock button 30 such that even if the operator presses the button 30, the AED 12 does not shock the patient.

Unfortunately, the soft package that contains the electrode pads 14a and 14b may delay the operator in setting up and activating the AED 12. Although the package protects the electrode pads 14a and 14b from moisture loss, it may fail to protect the electrode pads from shipping or handling damage caused by dropping, jostling, or crushing. Therefore, after the operator connects the electrode pads 14a and 14b to the AED 12—this step is unnecessary if the pads are preconnected—and opens the electrode-pad package, he/she may discover that the electrode pads are too damaged for use. Unfortunately, this damage to the electrode pads may delay the setting up and activation of the AED 12 because now the operator must disconnect and discard the damaged electrode pads, and retrieve, connect, and unpackage a new set of electrode pads.

Consequently, there is a need for a package that protects an electrode pad or electrode pads such as AED electrode pads from shipping and handling damage as well as from moisture loss. There is also a need for a system that eliminates the step of connecting an electrode pad or electrode pads such as AED electrode pads to a medical device such as an AED during an emergency.

SUMMARY OF THE INVENTION

A cartridge is provided for storing one or more electrode pads such as a defibrillator electrode pad. The cartridge includes a housing having a rigid portion, a storage space disposed within the housing, and a storage-space opening that allows one to remove/insert the electrode pad or electrode pads from/into the storage space.

Because it has a housing with a rigid portion, such a cartridge can better protect one or more electrode pads from shipping and handling damage. Furthermore, one can construct the cartridge such that it is attachable to a medical device such as an AED. This allows an operator to carry or store the medical device, cartridge, and one or more electrode pads as a single unit. In addition, one can construct the cartridge such that the one or more electrode pads can be pre-connected to the medical device. This can eliminate connecting the one or more electrode pads to the medical device during an emergency or when the medical-device operator is otherwise in a hurry. Furthermore, with pre-connected electrodes, the device can perform tests on the electrodes to ensure they are viable.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 2:
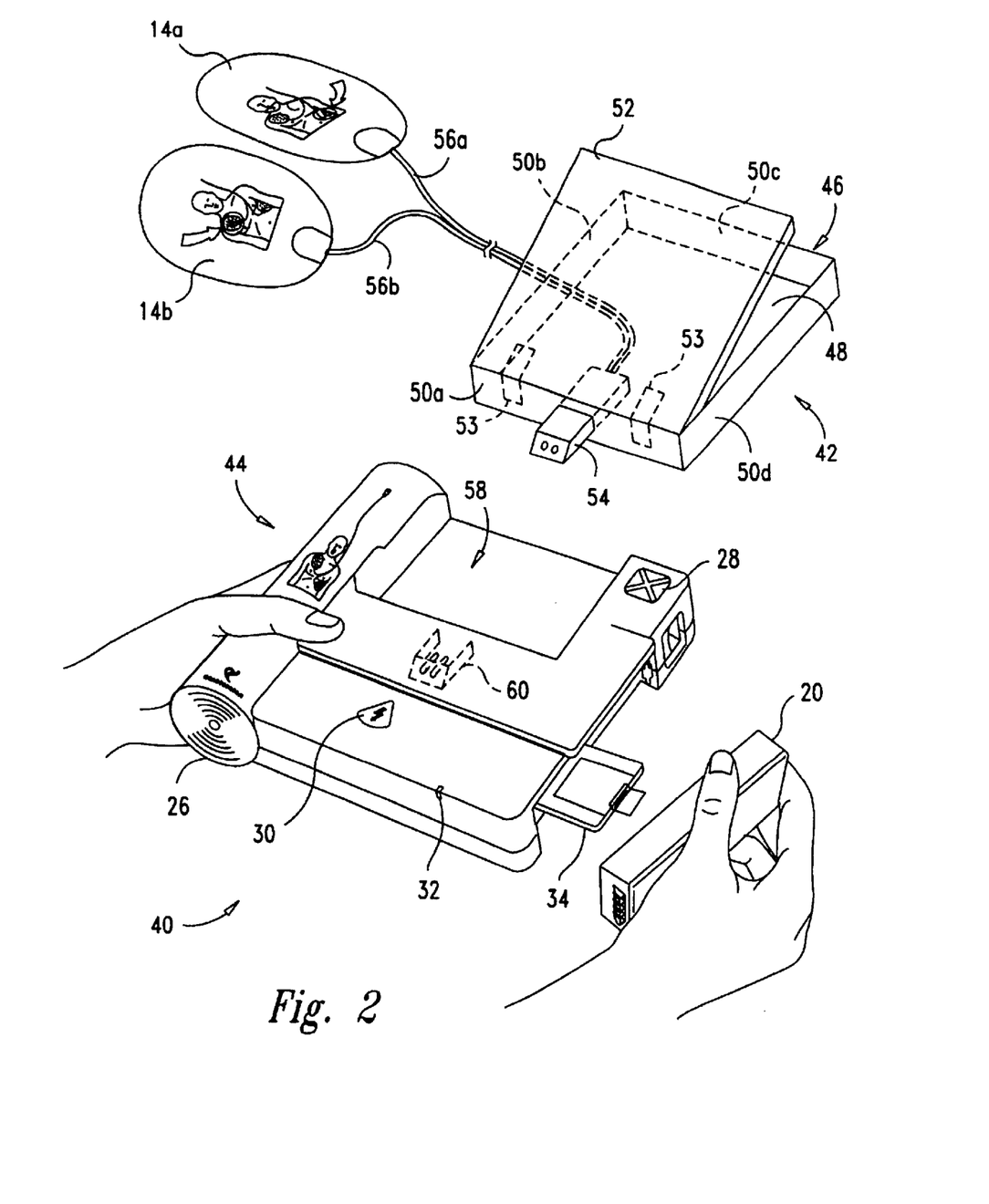
FIG. 2 is a perspective view of an AED system according to an embodiment of the invention.

FIG. 2 is a perspective view of an AED system 40, which includes a cartridge assembly 42 and an AED 44 according to an embodiment of the invention. For clarity, like numerals refer to elements common to the system 40 and the system 10 of FIG. 1. Furthermore, although the cartridge assembly 42 is discussed as including a pair of AED electrode pads 14a and 14b, the assembly 42 may include more or fewer electrode pads 14. In addition, although the cartridge assembly 42 is discussed as part of the AED system 40, the assembly 42 or a similar cartridge assembly can be used with other medical devices or systems such as a heart monitor (not shown). Thus, the electrode pads can be electrode pads suitable for defibrillation, monitoring cardioversion, pacing, or a combination thereof.

The cartridge assembly 42 includes electrode pads 14a and 14b and includes a rigid cartridge 46, which can protect the electrode pads 14a and 14b from handling damage better than a conventional soft package (not shown in FIG. 2) can. Furthermore, one can attach the cartridge 46 to the AED 44 so that he/she can carry or store the AED system 40 as a single unit, i.e., in one piece. In addition, in some embodiments the electrode pads 14a and 14b are attached to the cartridge 46 such that attaching the cartridge to the AED 44 also electrically connects the electrode pads to the AED 44. Thus, this simultaneous cartridge/pad connection often facilitates connecting the electrode pads 14a and 14b to the AED 44, and also facilitates deployment of the electrode pads during emergency usage of the AED system 40.

More specifically, the cartridge assembly 42 includes the cartridge 46 for storing the pads 14a and 14b. In one embodiment, the cartridge 46 has a rigid bottom, i.e., tray 48, rigid side walls 50a–50d, and a rigid lid 52, which is hinged to the side wall 50a with one or more hinges 53. The cartridge 46 may also include a conventional latch mechanism (not shown) for latching the lid 52 to one or more of the side walls 50a–50d. The tray 48, side walls 50a–50d, and the lid 52 can be formed from plastic or another rigid material. But in another embodiment, not all portions of the cartridge 46 are rigid. For example, only the tray 48 or the lid 52 may be rigid. Alternatively, the rigid portions of the cartridge 46 may be formed from a rigid framework such as the framework from which a milk crate is formed. The cartridge 46 might include an electrode-pad connector 54, which extends through the side wall 50a, helps secure the cartridge 46 to the AED 44, and electrically connects the electrode pads 14a and 14b to the AED 44 via electrode-pad wire leads 56a and 56b. The leads 56a and 56b are typically attached to the connector 54 via soldering, crimping or another conventional bonding technique. Although shown as a male connector, the connector 54 may be a female connector.

The AED 44 is similar to the AED 12 of FIG. 1 except that it includes a receptacle 58 and a connector 60 for respectively receiving the cartridge 46 and the connector 54. In an embodiment where not all portions of the cartridge 46 are rigid, the receptacle 58—which is typically formed as part of the rigid housing of the AED 44—may afford protection to the electrode pads 14a and 14b when the cartridge 46 is installed therein. Furthermore, although shown as a female connector, the connector 60 may be a male connector. In addition, although omitted from FIG. 2 for clarity, the AED 44 may include the on/off switch 22 and the display 24 of FIG. 1. But to accommodate the receptacle 58 and the connector 60, the locations of the switch 22 and the display 24 may be different from their respective locations on the AED 12.

In another embodiment, the AED 44 includes Velcro® strips (not shown) for attaching the cartridge 46 to the AED 44. In this embodiment, the receptacle 58 or the connectors 54 and 60 may be omitted. Alternatively, other techniques can be used for attaching the cartridge 46 to the AED 44.

Still referring to FIG. 2, the operation of the AED system 40 is discussed according to an embodiment of the invention. During an emergency where it is determined that a patient (not shown) may need a shock, the operator (hand shown in FIG. 2) retrieves the AED 44 and installs the battery 20 if it is not already installed. Next, the operator inserts the connector 54 into the connector 60, and thus inserts the cartridge 46 into the receptacle 58, if the cartridge 46 is not already installed. Then, the operator opens the lid 52 and removes the electrode pads 14a and 14b from the cartridge 46. Next, the operator activates the AED 44, and in response to displayed or spoken instructions, places the electrode pads 14a and 14b on the patient. The AED 44 then analyzes the patient's ECG to determine whether the patient is suffering from a shockable heart rhythm. If the AED 44 determines that the patient is suffering from a shockable heart rhythm, then it instructs the operator to depress the shock button 30. Conversely, if the AED 44 determines that the patient is not suffering from a shockable heart rhythm, it informs the operator to seek appropriate non-shock treatment for the patient and disables the shock button 30. After the operator has treated the patient, he/she removes the cartridge 46 from the receptacle 58 and inserts a new cartridge with new pads inside into the receptacle 58. In one embodiment, the AED 44 sounds a reminder if the operator does not install a new cartridge within a predetermined time of removing the cartridge 46, and continues to sound the reminder until a new cartridge is installed. Thus, with a new cartridge installed, the AED 44 is ready for its next use. Alternatively, one may wait until the next use of the AED 44 to install a new cartridge.

Figure 3:
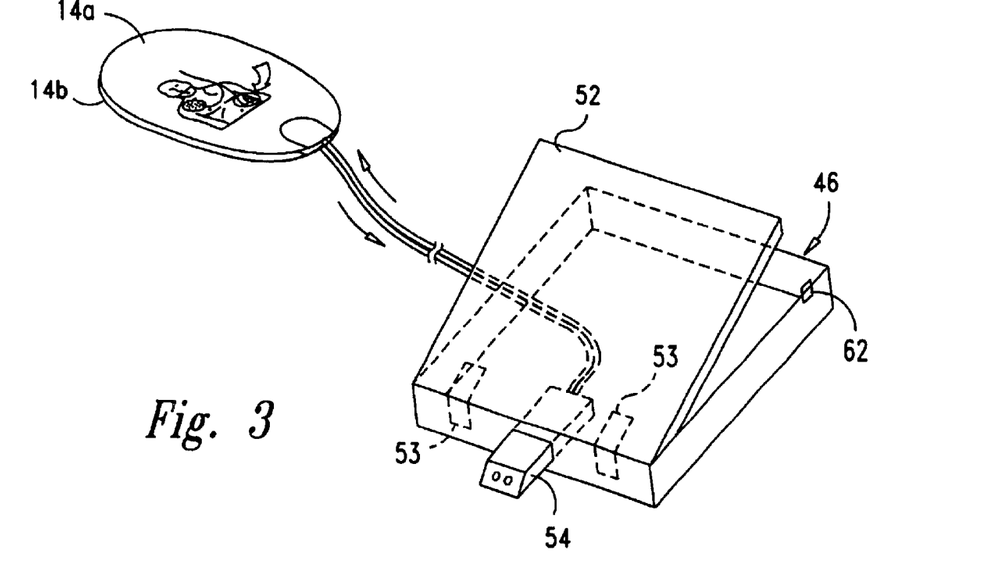
FIG. 3 is a perspective view of the cartridge assembly of FIG. 2 having an electrode-pad connector according to an embodiment of the invention.

FIG. 3 is a perspective view of the cartridge assembly 42 of FIG. 2 according to another embodiment of the invention. The assembly 42 of FIG. 3 is similar to the assembly 42 of FIG. 2 except that the cartridge 46 of FIG. 3 includes a conventional sensor 62—e.g., optical, mechanical, electrical—for indicating to the AED 44 (FIG. 2) whether the lid 52 is open or closed. The sensor 62 typically communicates with the AED 44 via the connector 54, but may employ other communication techniques such as optical or wireless communications. If the lid 52 is open while the AED system 40 (FIG. 2) is not being used, the AED 44 may periodically sound a reminder until one closes the lid. Alternatively, the AED 44 may use the sensor 62 to ensure that the lid 52 is closed during testing of the pads 14a and 14b. For example, the AED 44 may run a continuity test to ensure that the electrode pads 14a and 14b are properly connected to the AED 44 before an operator (not shown in FIG. 3) attaches them to a patient (not shown). Specifically, the electrode pads 14a and 14b may be packaged within the cartridge 46 such that they are electrically coupled to each other. The AED 44 drives the connector 60 (FIG. 2) with a test signal. If a current flows—the arrows show the direction of the current flow—into the connector 60, through the connector 54, the electrode pad 14a, and the electrode pad 14b, and back out from the connector 60, then the AED 44 determines that the electrode pads 14a and 14b—and thus the connector 54 and cartridge 46—are properly connected to the AED 44. Because the test may fail if the operator removes the electrode pads 14a and 14b from the cartridge 46, the AED 44 may display or sound a warning if the lid 52 is open, and may halt the test until the operator closes the lid. Alternately, the AED 44 may use the sensor 62 to insure that once the lid 52 has been opened, and the cartridge seal compromised, the user replaces the cartridge 46.

Figure 4:
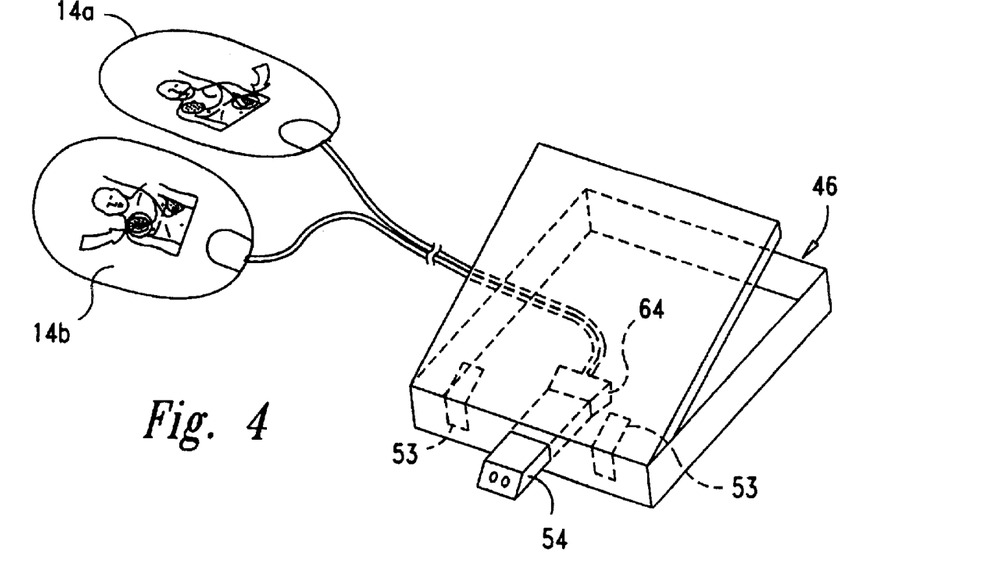
FIG. 4 is a perspective view of the cartridge assembly of FIG. 2 having an electrode-pad connector according to another embodiment of the invention.

FIG. 4 is a perspective view of the cartridge assembly 42 of FIG. 2 according to another embodiment of the invention. The assembly 42 of FIG. 4 is similar to the assembly 42 of FIG. 2 except that an electrode-pad connector 64 connects the electrode pads 14a and 14b to the connector 54. Consequently, the connector 64 allows an operator (not shown in FIG. 4) to easily connect/disconnect the electrode pads 14a and 14b to/from the cartridge 46. For example, assume that the AED 44 (FIG. 2) is intended for use by an unskilled operator who initially uses the AED 44 to revive a patient (not shown). When a paramedic (not shown) arrives, he/she may want to use a multifunctional defibrillator (not shown) such as a CodeMaster 100 manufactured by Agilent Technologies, to revive the patient. If the electrode pads 14a and 14b are hardwired to the connector 54 as in FIGS. 2 and 3, then the paramedic typically removes the electrode pads 14a and 14b from the patient, attaches new electrode pads to the patient, and connects the new electrode pads to the multifunctional defibrillator. Conversely, if the electrode pads 14a and 14b are connected to the connector 64, then the paramedic can merely unplug the connector 64 from the connector 54, and then plug the connector 64 into the multifunctional defibrillator without removing the electrode pads from the patient. This reduces the time it takes the paramedic to set up and use the multifunctional defibrillator on the patient.

Figure 5:
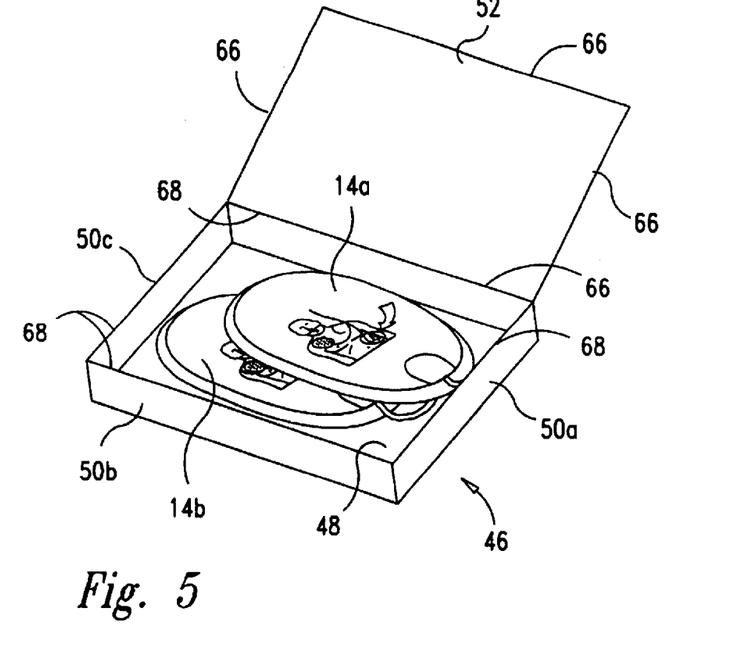
FIG. 5 is a perspective view of the cartridge assembly of FIG. 2 having a seal according to an embodiment of the invention.

FIG. 5 is a perspective view of an open cartridge 46 of FIG. 2, which would be sealed according to an embodiment of the invention. For clarity, the hinges 53 and the connector 54 are omitted from FIG. 5. The electrode pads 14a and 14b have a contact gel (not shown) that provides electrical conduction between a patient (not shown) and the electrode pads. If the electrode pads 14a and 14b are not properly sealed while packaged and stored, the gel may dry out. This reduces the electrical conduction between the electrode pads and the patient, and thus renders the electrode pads unusable. Therefore, the electrode pads 14a and 14b are typically sealed within the cartridge 46 to insure viability of the gel for a predetermined period, e.g., one year. Specifically, the outer edges 66 of the lid 52 are hermetically sealed to the respective upper edges 68 of the side walls 50a–50d. This hermetically sealed cartridge, which includes the tray 48, side walls 50a–50d, and lid 52 provide a moisture barrier sufficient to maintain the viability of the electrode-pad contact gel for the predetermined period. To break the hermetic seal and to gain access to the electrode pads 14a and 14b, one merely opens the lid 52. Materials that provide a sufficient moisture barrier and from which one may form the tray 48, side walls 50a–50d, and lid 52 are conventional and might include polymer resins such as polypropylene, polyethylene, or cyclic olefin co-polymer, such as Topas®, which is produced by Ticona.

Figure 6:
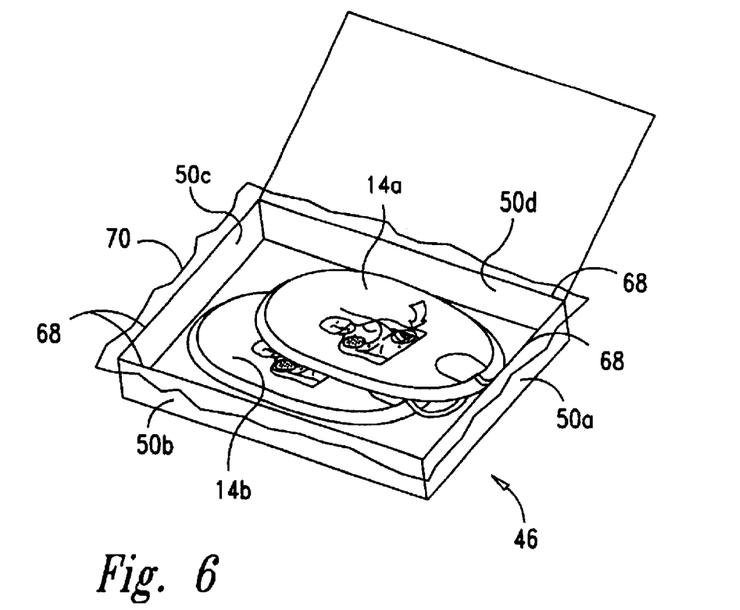
FIG. 6 is a perspective view of the cartridge assembly of FIG. 2 having a seal according to another embodiment of the invention.

FIG. 6 is a perspective view of an open cartridge 46 of FIG. 5, which is sealed according to another embodiment of the invention. In this embodiment, a sheet of material 70 is hermetically sealed to the edges 68 of the side walls 50a–50d. Together, the hermetic seal, tray 48, side walls 50a–50d, and material 70 provide a moisture barrier sufficient to maintain the viability of the electrode-pad contact gel for the predetermined period. To break the hermetic seal and to gain access to the electrode pads 14a and 14b, one merely opens the lid 52 and peels off the material 70. In one embodiment, the material 70 is transparent to allow the operator to see if the electrode pads 14a and 14b are appropriate for a patient (not shown) before removing the material 70. For example, if the electrode pads 14a and 14b are adult pads and the patient is an adult, then the electrode pads are appropriate for the patient. Conversely, if the electrode pads 14a and 14b are adult pads and the patient is a child, then the electrode pads are inappropriate for the patient. Thus, if the electrode pads 14a and 14b are inappropriate, they remain sealed and can be later used on another patient. Materials that provide a sufficient moisture barrier and from which one may form the sheet 70 include polypropylene, polyethylene, Topas®, Aclar®, which is produced by Honeywell, partially metallic clear film like the anti-static film used to package static-sensitive semiconductor components, and a metal foil film.

Figure 7:
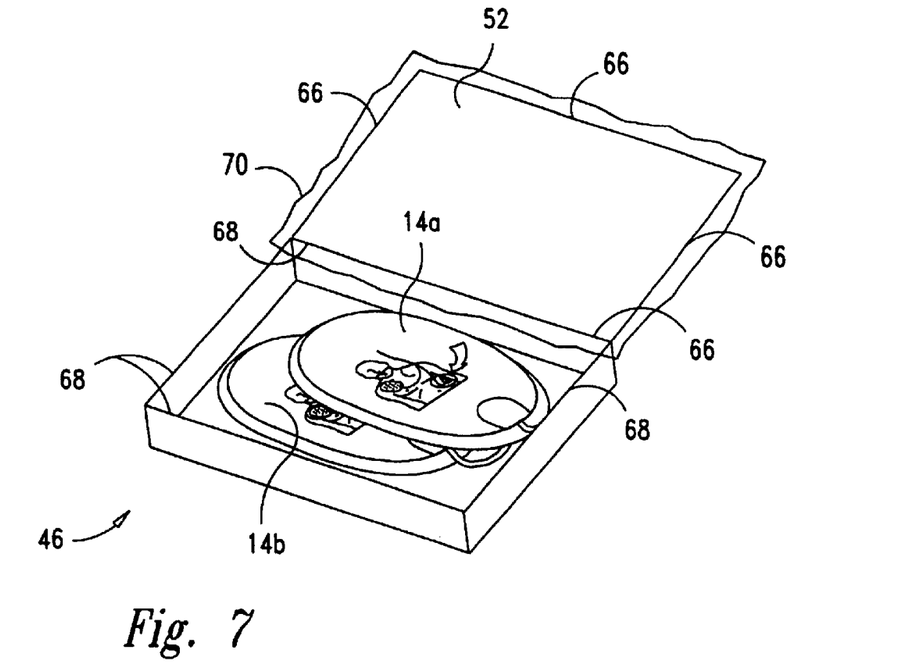
FIG. 7 is a perspective view of the cartridge assembly of FIG. 2 having a seal according to another embodiment of the invention.

FIG. 7 is a perspective view of the cartridge 46 of FIG. 6, which is sealed according to another embodiment of the invention. In this embodiment, the sheet of material 70 is hermetically sealed to the lid 52 and to the edges 68 of the side walls 50a–50d. Together, the seal, tray 48, side walls 50a–50d, and material 70 provide a moisture barrier sufficient to maintain the viability of the electrode-pad contact gel for the predetermined period. The lid 52 also contributes to the moisture barrier, particularly if the material 70 is sealed to the edges 66 of the lid 52. In one embodiment, the seal between the material 70 and the lid 52 is stronger than the seals between the material 70 and the side-wall edges 68. This causes the material to peel away from the side-wall edges 68 and continue sticking to the lid 52 when one opens the lid to break the seal and gain access to the electrode pads 14a and 14b. This keeps the material 70 from "floating" around and potentially interfering with the rescue operation. Alternatively, the seal between the material 70 and the lid 52 may be weaker than the seals between the material 70 and the side-wall edges 68. This causes the material to remain attached to the side-wall edges 68 when one opens the lid 52. One then peels away the material 70 as discussed above in conjunction with FIG. 6 to break the seal and gain access to the electrode pads 14a and 14b.

Referring to FIGS. 6–7, in another embodiment, a first sheet of material 70 lines the interior of the cartridge 46 and overhangs the edges 68 of the side walls 50a–50d, and a second sheet of material 70 lines the inner side of the lid 52 and overhangs the edges 66 of the lid 52. These two sheets 70 are hermetically or otherwise sealed together along the respective overhanging edges to form a moisture barrier for the electrode pads 14a and 14b stored in the cartridge 46. One opens the cartridge by opening the lid and detaching the top sheet 70 from the bottom sheet 70. Alternatively, one can tear the top sheet 70 open, or the top sheet 70 can be attached to the inner side of the lid 52 such that opening the lid 52 detaches the top sheet 70 from the bottom sheet 70.

Figure 8:
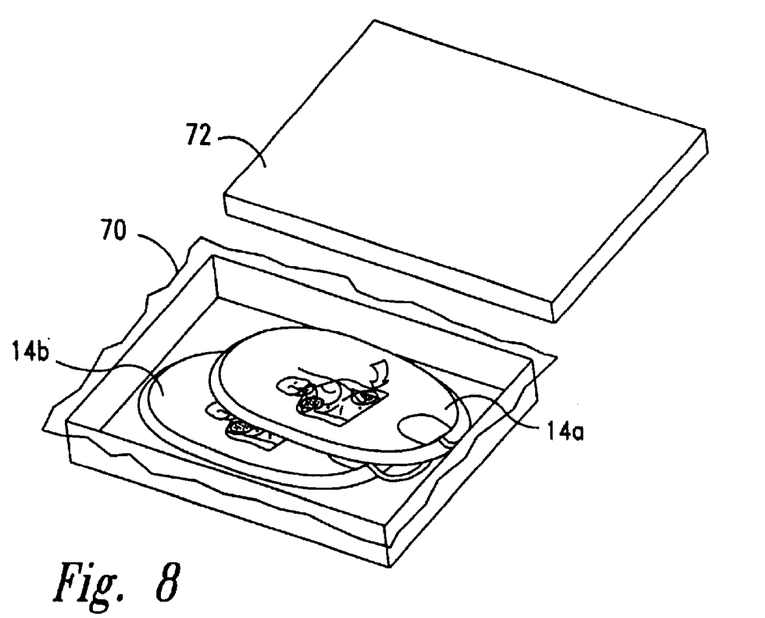
FIG. 8 is a perspective view of the cartridge assembly of FIG. 7 having a sliding lid according to an embodiment of the invention.

FIG. 8 is a perspective view of the cartridge 46 of FIG. 6, which is sealed with the sheet 70 as discussed above in conjunction with FIG. 6 but which includes a sliding lid 72 instead of the hinged lid 52 (FIG. 6).

Figure 9:
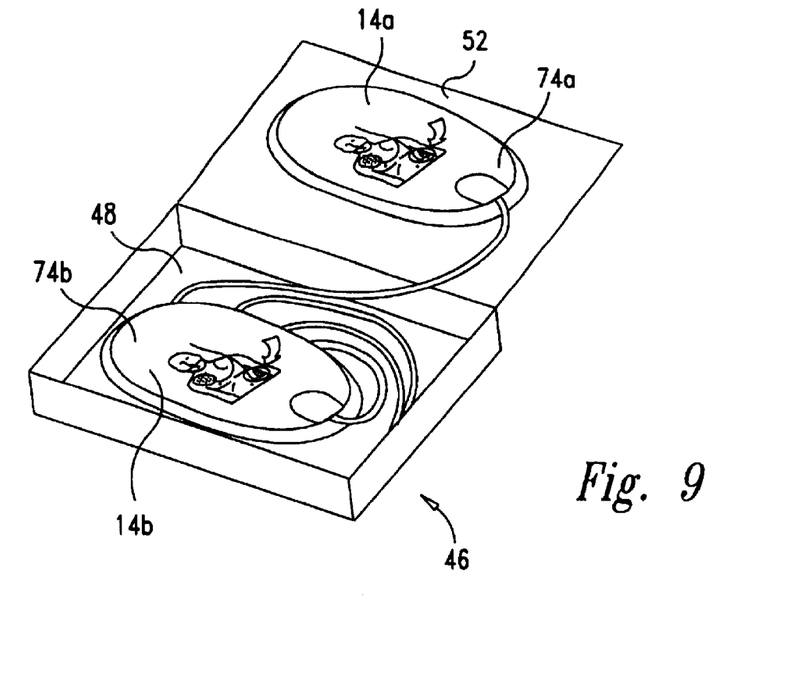
FIG. 9 is a perspective view of the cartridge assembly of FIG. 2 where the electrode-pads are sealed to the sides of the cartridge according to an embodiment of the invention.

FIG. 9 is a perspective view of the cartridge 46 of FIG. 5 where the electrode pads 14a and 14b are sealed to the cartridge according to an embodiment of the invention. The conductive side of the electrode pad 14a faces and is hermetically sealed to the inside of the lid 52. Together, the lid 52, the metal layer of the electrode pad 14a and the adhesive on the dielectric layer 74 provide a moisture barrier sufficient to maintain the viability of the electrode-pad contact gel for the predetermined period. Similarly, the conductive side of the electrode pad 14b faces and is hermetically sealed to the inside of the tray 48 such that the tray 48, the metal layer of the electrode-pad 14b, and the adhesive on the dielectric layer 74b provide a moisture barrier sufficient to maintain the viability of the electrode-pad contact gel for the predetermined period. Therefore, one peels the electrode pads 14a and 14b from the lid 52 and the tray 48, respectively, and then attaches them to the patient (not shown). Consequently, the adhesive that seals the electrode pads 14a and 14b to the lid 52 and the tray 48 may help hold the electrode pads to the patient. Suitable materials for the pad dielectrics 74a and 74b may include polypropylene, polyethylene, Topas®, Aclar®, partially metallic film, and a metal foil film.

Figure 10:
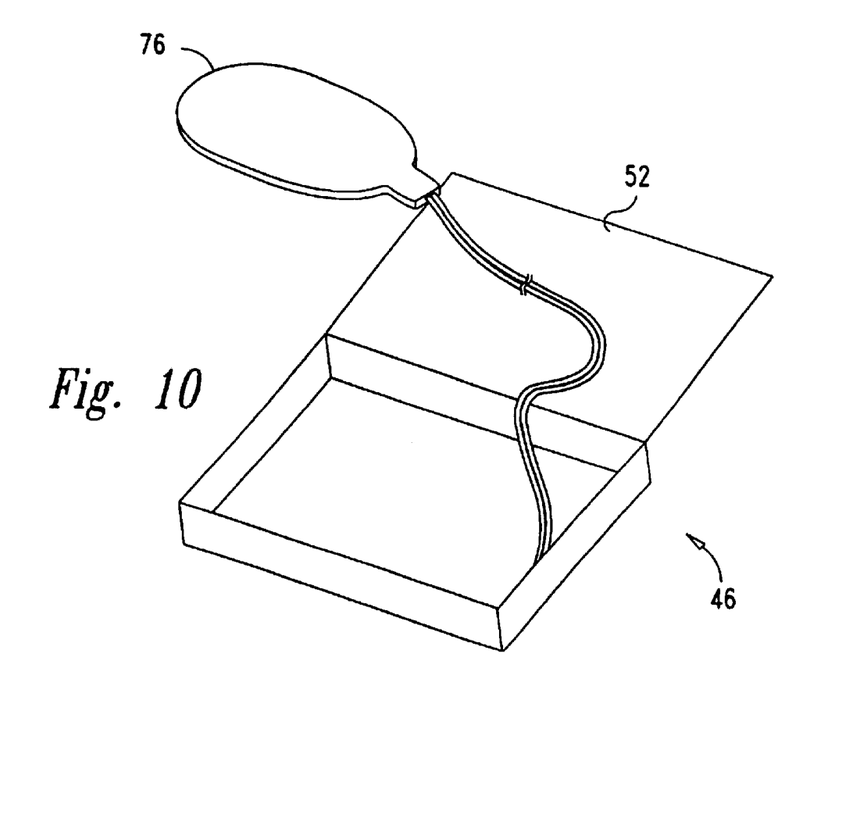
FIG. 10 is a perspective view of the cartridge assembly of FIG. 2 where the electrode-pads are sealed within a soft package according to an embodiment of the invention.

FIG. 10 is a perspective view of the cartridge 46 of FIG. 5 where the electrode pads 14a and 14b (not shown in FIG. 10) are sealed within the cartridge according to an embodiment of the invention. The electrode pads 14a and 14b are sealed within a conventional soft package 76, which is stored inside the cartridge 46. The sealed soft package provides a moisture barrier sufficient to maintain the viability of the electrode-pad contact gel for a predetermined period. Alternatively, the cartridge 46 can be sealed as discussed above in conjunction with FIGS. 5–8 to enhance the moisture barrier or to provide a back-up moisture barrier in the event that the seal of the package 76 fails. To gain access to the electrode pads 14a and 14b, one opens the lid 52 of the cartridge 46 and removes and opens the package 76. He/she can then attach the electrode pads 14a and 14b to the patient (not shown). Suitable materials for the package 76 include polypropylene, polyethylene, Topas®, Aclar®, partially metallic film, and a metal foil film.

Referring to FIGS. 2–10, one may form the cartridge 46 using conventional manufacturing techniques.

In one embodiment, the cartridge 46 is injection molded. For example, the tray 48, side walls 50a–50d, and connector 54 can be molded as a first integral piece and the lid 52 molded as a second piece, which is later attached to the side wall 50a with the hinges 53. Alternatively, the tray 48, side walls 50a–50d, lid 52, and connector 54 can be molded as a single piece with a membrane (not shown) acting as a hinge between the side wall 50d and the lid 52. Or, one can position a preformed hinge 53, connector 54, or other component such as a printed-circuit board (not shown) into the mold (not shown), and then inject the cartridge-forming material into the mold such that the preformed hinge 53, connector 54, or other component becomes embedded in the cartridge 46. As discussed above in conjunction with FIG. 5, suitable cartridge-forming materials include plastics such as polypropylene, polyethylene, or Topas®. Alternatively, one may mold the cartridge 46 from a softer, more resilient material such as rubber such that the cartridge 46 is less likely to suffer damage if it is dropped, stepped on, or otherwise jostled.

In another embodiment, the tray 48 and the side walls 50a–50d may be thermoformed. Thermoforming entails heating a sheet of material such as plastic to its softening point. A vacuum and/or pressure is applied to the softened material and it is formed into the shape of the lidless cartridge 46. One may form the lid 52 by injection molding or other conventional manufacturing technique. Although thermoforming is often less expensive than injection molding, one cannot easily insert preformed components, such as the connector 54, through the walls of the cartridge 46.

Still referring to FIGS. 2–10, one can use other manufacturing techniques to form the cartridge 46, such as metal injection molding, injection blow molding, compression molding, or die casting.

Figure 11:
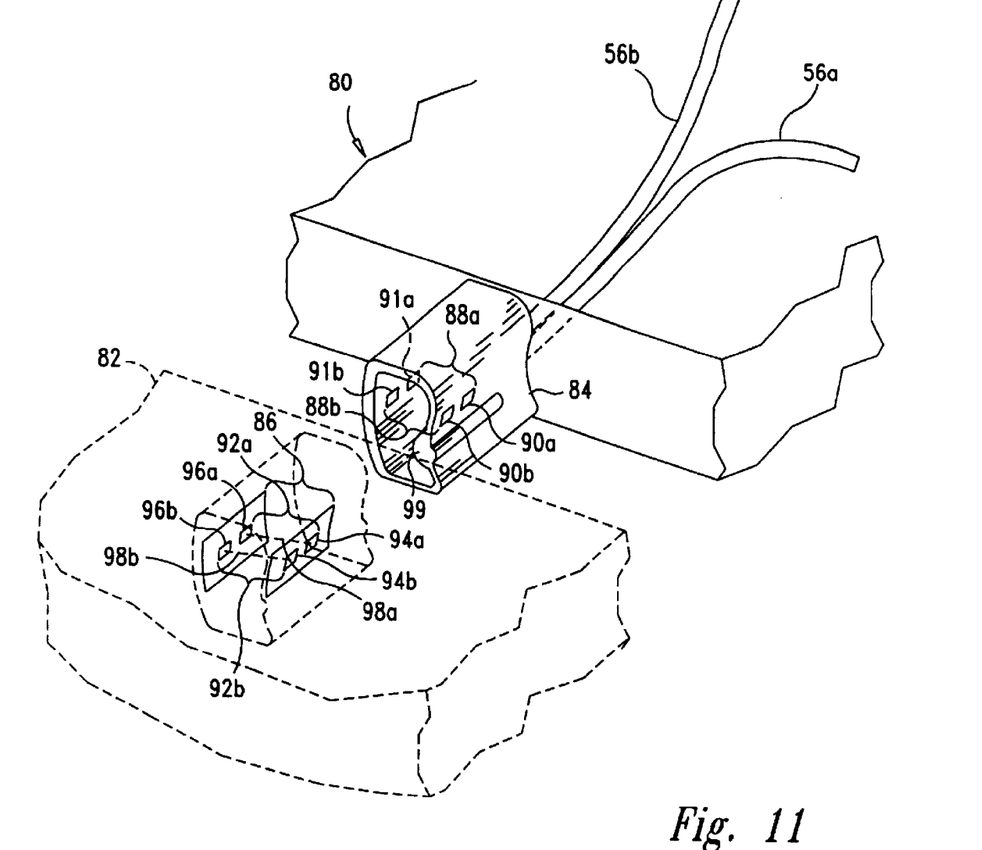
FIG. 11 is a perspective view of a smart cartridge connector and receptacle according to an embodiment of the invention.

FIG. 11 is a partial perspective view of a "smart" cartridge 80 and a compatible AED 82, which respectively include a "smart" connector 84 and a reading connector 86 according to an embodiment of the invention. The connector 84 provides information to the AED 82, and the connector 86 receives the connector 84 and reads the provided information. For example, the connector 84 may indicate the type of electrode pads 14a and 14b (not shown in FIG. 11) contained within the cartridge 80. The AED 82 determines the type of electrode pads that are contained within the cartridge. It can then communicate this information to the user of the AED (with voice or visual prompts). Consequently, the ability of the AED 82 to determine the electrode-pad type prevents the patient from receiving potentially dangerous or ineffective treatment caused by the use of improper electrode pads, and assists an unskilled operator who may not know whether the electrode pads within the cartridge 80 are the proper type.

More specifically, the connector 84 codes the desired information using any one of a number of conventional coding techniques. In the illustrated embodiment, the connector 84 includes two sets 88a and 88b of two optical windows 90a and 91a and 90b and 91b, respectively. The windows 90a and 91a within the set 88a and the windows 90b and 91b within the set 88b may be transparent or opaque. Therefore, the sets 88a and 88b act as two bits that can code up to four states: 1) both sets transparent, 2) 88a transparent and 88b opaque, 3) 88a opaque and 88b transparent, and 4) both sets opaque. For example, state 1) may indicate that the cartridge 80 contains adult pads, state 2) may indicate that the cartridge 80 contains pediatric pads, and states 3) and 4) may be unused.

The connector 86 decodes the information provided by the connector 84. In the illustrated embodiment, the connector 86 includes two optical generator/sensor pairs 92a and 92b, which each include a respective optical-signal generator 94a and 94b, such as a photodiode, and an optical sensor 96a and 96b. The generators 94a and 94b generate respective optical beams 98a and 98b. While the connector 84 is within the connector 86, if the windows 90a and 91a of the set 88a are transparent, then the optical beam 98a propagates through the windows 90a and 91a, and, consequently, the sensor 96a senses the beam 98a. Conversely, if the windows 90a and 91a are opaque, then the optical beam 98a does not propagate through the windows 90a and 91a, and, consequently, the sensor 96a does not sense the beam 98a. One can make the same analysis for the windows 90b and 91b of the set 88b, the sensor 96b, and the beam 98b. Therefore, the connector 86 recognizes the above states 1)–4) as follows: 1) both sensors 96a and 96b respectively receive the beams 98a and 98b, 2) the sensor 96a receives the beam 98a, the sensor 96b does not receive the beam 98b, 3) the sensor 96a does not receive the beam 98a, the sensor 96b receives the beam 98b, and 4) both sensors 96a and 96b respectively do not receive the beams 98a and 98b. The AED 82 can then take a preprogrammed course of action in response to the decoded state.

Still referring to FIG. 11 during an emergency where it is determined that a patient may need a shock, the operator retrieves the AED 82 and inserts the connector 84 into the connector 86 if the cartridge 80 is not already installed in the AED 82. Then the operator conventionally enters the type of patient—adult or child for example—into the AED 82. In response to the information coded by the connector 84 and decoded by the connector 86, the AED 82 determines whether the cartridge 80 contains the appropriate electrode pads for the patient. If the AED 82 determines that the cartridge 80 does contain the appropriate pads, then it instructs the operator to continue with the rescue effort. If the AED 82 determines that the cartridge 80 does not contain the appropriate electrode pads, then it instructs the operator to remove the cartridge 80 and to install another cartridge that contains the appropriate electrode pads. The AED 82 may disable the shock button 30 (FIG. 2) until the operator installs a cartridge containing the appropriate pads.

Although they are described as respectively coding and decoding information optically, the connectors 84 and 86 may use other conventional coding and decoding techniques. For example, a protrusion 99 may code information that the connector 86 can decode. Examples of other such techniques are disclosed in U.S. patent app. Ser. No. 09/574,688, entitled "Smart Medical Connector System and Method of Use," filed May 17, 2000, which is incorporated by reference.

Figure 12:
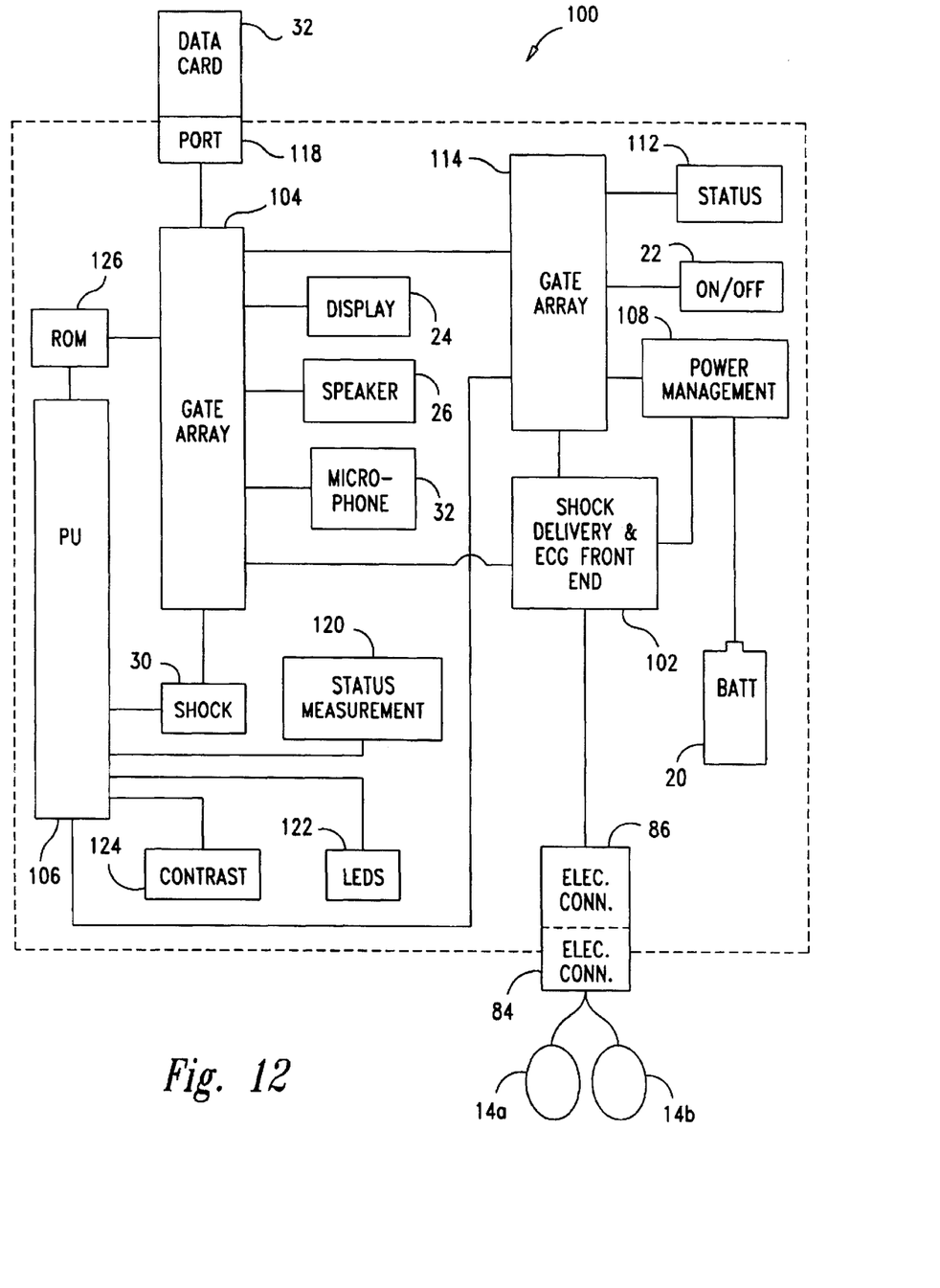
FIG. 12 is a block diagram of an AED circuit that the AED of FIG. 2 incorporates according to an embodiment of the invention.

FIG. 12 is a block diagram of an AED circuit 100, which the AED 44 of FIG. 2 or the AED 82 of FIG. 11 can incorporate according to an embodiment of the invention. The electrode pads 14a and 14b are coupled to the circuit 100 via the connectors 84 and 86—or the connectors 54 and 60 (FIG. 2) if the circuit 100 is unable to interpret information from a smart cartridge—and are operable to sense a patient's ECG and to apply an electrical shock to the patient. A shock-delivery-and-ECG front-end circuit 102 samples the patient's ECG during an analysis mode of operation and provides a shock to the patient via the connectors 84 and 86 and the electrode pads 14a and 14b during a shock-delivery mode of operation. A gate array 104 receives the ECG samples from the circuit 102 and provides them to a processor unit (PU) 106, which stores and analyzes the samples. If analysis of the patient's ECG indicates that the patient is suffering from a shockable heart rhythm, then the processor unit 106 instructs the circuit 102 via the gate array 104 to enable delivery of a shock to the patient when an operator (not shown in FIG. 12) presses the shock button 30. Conversely, if analysis of the patient's ECG indicates that the patient is not suffering from a shockable heart rhythm, then the processor unit 106 effectively disables the shock button 30 by preventing the circuit 102 from delivering a shock to the patient when the operator presses the shock button.

Still referring to FIG. 12, the circuit 100 includes a power-management circuit 108 for distributing power from the battery 20 to the subcircuits of the circuit 100. The on/off switch 22 turns the circuit 100 "on" and "off", a status circuit 112 indicates the status of the circuit 100, and a gate array 114 interfaces the power-management circuit 108, the on/off circuit 22, and the status circuit 112 to the circuit 102, the processor unit 106, and the gate array 104. As discussed above in conjunction with FIG. 1, the AED 44 may include a display 24, which presents information to an operator, a speaker 26, which may provide audio instructions to the operator, and a microphone 32, which may record the operator's voice and other audible sounds. The data card 32 is connected to the gate array 104 via a port 118. The card 116 may store the operator's voice and other sounds along with the patient's ECG and a record of AED events for later study. A status-measurement circuit 120 provides the status of the circuit 100 subcircuits to the processor unit 106, and LEDs 122 provide information to the operator such as whether the processor unit 106 has enabled the circuit 102 to deliver a shock to the patient. A contrast button 124 allows the operator to control the contrast of the display screen 24 if present, and a memory such as a read only memory (ROM) 126 stores programming information for the processor unit 106 and the gate arrays 104 and 114.

The AED circuit 100 and other AED circuits are further discussed in the following references, which are incorporated by reference: U.S. Pat. No. 5,836,993, U.S. Pat. No. 5,735,879 entitled ELECTROTHERAPY METHOD AND APPARATUS, U.S. Pat. No. 5,607,454 entitled ELECTRO- THERAPY METHOD AND APPARATUS, and U.S. Pat. No. 5,879,374 entitled DEFIBRILLATOR WITH SELF-TEST FEATURES.

What is claimed:

1. A cartridge for storing an electrode pad the cartridge comprising:
   a housing having a rigid portion;
   a storage space disposed within the housing;
   a storage space opening operable to allow removal of the electrode pad from the storage space and insertion of the electrode pad into the storage space; and
   an electrode-pad connector that extends through the housing, that has a first end disposed outside of the housing and operable to connect to a medical device, and that has a second end disposed within the storage space and operable to connect to the electrode pad,
   wherein the housing comprises:
      a rigid tray having edges;
      rigid side walls attached to the edges of the tray;
      a rigid lid; and
      a hinge coupled to the rigid lid and to one of the rigid side walls.

2. The cartridge of claim 1 wherein the rigid portion comprises plastic.

3. The cartridge of claim 1 wherein the rigid portion comprises rubber.

4. The cartridge of claim 1 wherein the rigid portion comprises metal.

5. The cartridge of claim 1 wherein the rigid portion comprises ceramic.

6. The cartridge of claim 1 comprising a lid and a sheet of film operable to cover the storage space opening.

7. The cartridge of claim 1, further comprising:
   a sensor coupled to the housing and operable to indicate whether the lid is in an opened or closed position.

8. The cartridge of claim 1 wherein the housing is attachable to a medical device.

9. The cartridge of claim 1 wherein the housing is attachable to a defibrillator.

10. The cartridge of claim 1, further comprising electrode pad leads, of the electrode pad, said electrode pad leads directly connected to the electrode pad connector.

11. The cartridge of claim 10 further comprising a removable connector wherein said electrode pad leads of the electrode pad are connected to said removable connector, said removable connector being operable to connect in the electrode pad connector.

* * * * *